United States Patent [19]

Cook

[11] 4,087,404
[45] May 2, 1978

[54] POLYMERS STABILIZED WITH SUBSTITUTED 2-(PIPERIDINYL-4')-ETHYL ALCOHOL AND SALTS THEREOF

[75] Inventor: Barry Cook, Flixton, England

[73] Assignee: Ciba-Geigy Corporation, Ardsley, N.Y.

[21] Appl. No.: 687,790

[22] Filed: May 19, 1976

Related U.S. Application Data

[62] Division of Ser. No. 438,808, Feb. 1, 1974, Pat. No. 3,959,291.

[30] Foreign Application Priority Data

Feb. 3, 1973 United Kingdom ............... 5470/73

[51] Int. Cl.² .................... C08K 5/34; C07D 211/22
[52] U.S. Cl. ............................ 260/45.8 N; 106/171; 106/176; 260/293.66; 260/293.84; 260/293.9
[58] Field of Search .................. 260/45.8 N; 106/176

[56] References Cited

FOREIGN PATENT DOCUMENTS 1,398,412  6/1975  United Kingdom.
1,398,414  6/1975  United Kingdom.

OTHER PUBLICATIONS

Levkoeva, et al., Khim.-Farm. Zh. 5(9), 16–21, (1971).

Primary Examiner—H.S. Cockeram
Attorney, Agent, or Firm—Vincent J. Cavalieri

[57] ABSTRACT

A composition comprising an organic material and, as stabiliser, a compound having the formula

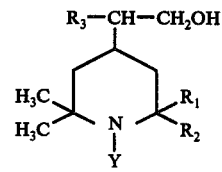

and salts thereof, wherein $R_1$ and $R_2$ are the same or different and each is an alkyl residue having from 1 to 12 carbon atoms or $R_1$ and $R_2$, together with the carbon atom to which they are bound, form a cycloalkyl residue having from 5 to 12 carbon atoms in the ring, Y is 0, hydrogen, a straight- or branched alkyl residue having from 1 to 20 carbon atoms, an alkenyl or alkynyl residue having from 3 to 12 carbon atoms, an aralkyl residue having from 7 to 12 carbon atoms or a group having the formula

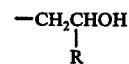

wherein R is hydrogen, or a methyl or phenyl residue and $R_3$ is hydrogen or a straight- or branched chain alkyl residue having from 1 to 12 carbon atoms.

13 Claims, No Drawings

POLYMERS STABILIZED WITH SUBSTITUTED 2-(PIPERIDINYL-4')-ETHYL ALCOHOL AND SALTS THEREOF

This is a divisional of application Ser. No. 438,808 filed on Feb. 1, 1974, now U.S. Pat. No. 3,959,291.

The present invention relates to new chemical compounds and in particular to new derivatives of substituted 2-(piperidinyl-4')-ethyl alcohol.

According to the present invention, there is provided a composition comprising an organic material and, as stabilisers, a compound having the formula:

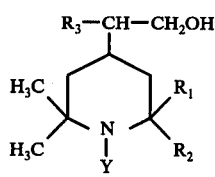
I and salts thereof, wherein $R_1$ and $R_2$ are the same or different and each is an alkyl residue having from 1 to 12 carbon atoms, or $R_1$ and $R_2$, together with the carbon atom to which they are bound, form a cycloalkyl residue having from 5 to 12 carbon atoms in the ring, Y is O, hydrogen, a straight- or branched alkyl residue having from 1 to 20 carbon atoms, an alkenyl or alkynyl residue having from 3 to 12 carbon atoms, an aralkyl residue having from 7 to 12 carbon atoms or a group having the formula:

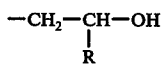

wherein R is hydrogen, or a methyl or phenyl residue, and $R_3$ is hydrogen, or a straight- or branched chain alkyl residue having from 1 to 12 carbon atoms.

When $R_1$ and/or $R_2$ is an alkyl residue, examples of such residues are methyl, ethyl, n-propyl, isopropyl, n-butyl, sec-butyl, n-hexyl and n-dodecyl residues; preferably however $R_1$ and/or $R_2$ is an alkyl residue having from 1 to 4 carbon atoms and most preferably, $R_1$ and $R_2$ are each a methyl residue.

When $R_1$ and $R_2$, together with the carbon atom to which they are bound form a cycloalkyl residue, examples of preferred structures are those having the formula:

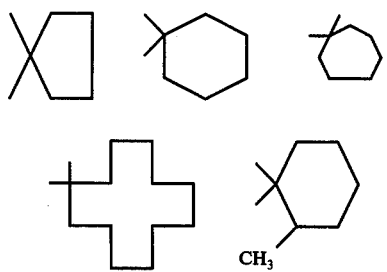

Apart from O, examples of preferred substituents Y are hydrogen, methyl, ethyl, n-propyl, n-butyl, n-hexyl, n-octadecyl, octadecyl, allyl, α-methallyl, 10-undecenyl, propargyl, benzyl, α-methylbenzyl, p-methylbenzyl, α,p-dimethylbenzyl, 2-hydroxyethyl, 2-hydroxypropyl and 2-hydroxy-2-phenylethyl residues. Particularly preferred substituents Y are straight- or branched alkyl residues having from 1 to 4 carbon atoms, especially the methyl residue, hydrogen and O.

Examples of substituents $R_3$, apart from hydrogen, are methyl, ethyl, n-propyl, isopropyl, n-butyl, sec-butyl, n-hexyl and n-dodecyl residues. Preferred alkyl residues $R_3$ are those having from 1 to 4 carbon atoms and the most preferred substituent $R_3$ is hydrogen.

Suitable examples of salts of the compounds of formula I useful in the present invention include salts of inorganic acids such as phosphates, carbonates and chlorides as well as salts of organic acids such as acetates, stearates, maleates, citrates, tartrates, oxalates, benzoates and substituted carbamic acids.

Specific examples of preferred compounds of formula I include the following:

2-(2',2',6',6'-Tetramethylpiperidinyl-4'-)ethyl alcohol
2-(1'-Oxyl-2',2',6',6'-tetramethylpiperidinyl-4')-ethyl alcohol
2-(1',2',2',6',6'-Pentamethylpiperidinyl-4')-ethyl alcohol
2-(n-Butyl)-2-(2',2',6'6'-tetramethylpiperidinyl-4')-ethyl alcohol
2-(n-Octyl)-2-(2',2',6',6'-tetramethylpiperidinyl-4')-ethyl alcohol
2-(n-Dodecyl)-2-(2',2',6',6'-tetramethylpiperidinyl-4')-ethyl alcohol
2-(Isopropyl)-2-(2',2',6',6'-tetramethylpiperidinyl-4')-ethyl alcohol
2-(1'-Ethyl-2',2',6',6'-tetramethylpiperidinyl-4')-ethyl alcohol
2-(1'-sec-Butyl-2',2',6',6'-tetramethylpiperidinyl-4')-ethyl alcohol
2-(1'-n-Butyl-2',2',6',6'-tetramethylpiperidinyl-4')-ethyl alcohol
2-(1'-n-Hexyl-2',2',6',6'-tetramethylpiperidinyl-4')-ethyl alcohol
2-(1'-n-Dodecyl-2',2',6',6'-tetramethylpiperidinyl-4')-ethyl alcohol
2-(1'-Eicosyl-2',2',6',6'-tetramethylpiperidinyl-4')-ethyl alcohol
2-(1'-Allyl-2',2',6',6'-tetramethylpiperidinyl-4')-ethyl alcohol
2-(1'-α-Methallyl-2',2',6',6'-tetramethylpiperidinyl-4')-ethyl alcohol
2-(1'-Propargyl-2',2',6',6'-tetramethylpiperidinyl-4')-ethyl alcohol
2-(1'-Benzyl-2',2',6',6'-tetramethylpiperidinyl-4')-ethyl alcohol
2-[1'-(α-Methylbenzyl)-2',2',6',6'-tetramethylpiperidinyl-4']-ethyl alcohol
2-[1'-(2''-Hydroxyethyl)-2',2',6',6'-tetramethylpiperidinyl-4']-ethyl alcohol
2-(2',2'-di-Isopropyl-6',6'-dimethylpiperidinyl-4')-ethyl alcohol
2-(2',2'-Diethyl-6',6'-dimethylpiperidinyl-4')-ethyl alcohol
2-(1',2',6',6'-Tetramethyl-2'-n-propylpiperidinyl-4')-ethyl alcohol
2-(1'-aza-2',2'-dimethylspiro[5',5']undecyl-4')-ethyl alcohol.

The compounds of this invention provide protection to polymers against deterioration caused by visible and/or ultraviolet light and that caused by oxidation degradation and that caused by thermal effects.

Compounds of Formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methyl-butene-1, hexene-1, 4-methylpentene-1, 4-methylhexene-1 and 4,4-dimethyl-pentene-1, and also co- and ter-polymers of olefines, particularly of ethylene or propylene.

Other organic materials susceptible to degradation by the effects of light and the properties of which are improved by the incorporation therein of a compound of Formula I include natural and synthetic polymeric materials, for instance natural and synthetic rubbers, the latter including, for example, homo-, co- and ter-polymers of acrylonitrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamides; urea-formaldehyde and melamine-formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound of formula I may be added to the polymer during the preparation of the latter, for instance at the latex stage of polymer production, to provide pre-stabilised polymer material.

The compounds of formula I may also be added to the polymeric material as a reactive ingredient as for example in polyesters or polyurethanes.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabiliser of formula I together with one or more functional additives for polymers.

Examples of suitable antioxidants are those of the hindered phenol type such as those selected from the following groups:

(1) Phenolic compounds having the general formula

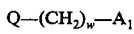
$$Q-(CH_2)_w-A_1$$

wherein
Q is

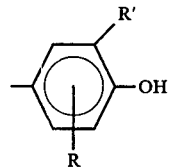

$A_1$ is $$CR(COOR'')_2$$

or

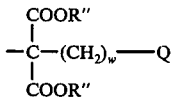

R is hydrogen or lower alkyl
R' is lower alkyl
R'' is alkyl group having from 6–24 carbon atoms
W is 0 or an integer from 1 to 4.

Illustrative examples of the compounds shown above are: di-n-octadecyl α-(3,5-di-t-butyl-4-hydroxy-benzyl)-malonate di-n-octadecyl α-(3-t-butyl-4-hydroxy-5-methyl-benzyl) malonate which is disclosed in the Netherlands Patent Specification No. 6,711,199, February, 19th, 1968 di-n-octadecyl-α,α'bis-(3-t-butyl-4-hydroxy-5-methylbenzyl) malonate which is disclosed in the Netherlands Patent Specification No. 6,803,498, September, 18th, 1968

(2) Phenolic compounds having the general formula

$$Q-R'''$$

wherein
Q is as hereinbefore defined, and
R''' is as hereinafter defined.

Illustrative examples of the compounds shown above are
2,6-di-t-butyl-p-cresol
2-methyl-4,6-di-t-butylphenol and the like.
2,6-di-Octadecyl-p-cresol.

(3) Phenolic compounds having the formula

$$Q-C_wH_{2w}-Q$$

wherein Q and w are as hereinbefore defined, such as 2,2′-methylene-bis(6-t-butyl-4-methylphenol)
2,2′-methylene-bis-(6-t-butyl-4-ethylphenol)
4,4′-butylidene-bis(2,6-di-t-butylphenol)
4,4′-(2-butylidene)-bis(2-t-butyl-5-methylphenol)
2,2′-methylene-bis[6-(2-t-methylcyclohexyl)-4-methylphenol
2,2′-methylene-bis(3-t-butyl-5-ethylphenol)
4,4′-methylene-bis(3,5-di-t-butylphenol)
4,4′-methylene-bis(3-t-butyl-5-methylphenol)
2,2′-methylene-bis(3-t-butyl)-5-methylphenol).

(4) Phenolic compounds having the formula

wherein
Q is as hereinbefore defined and
R‴ is as hereinafter defined.
Illustrative examples of such compounds are
2,5-di-t-butylhydroquinone
2,6-di-t-butylhydroquinone
2,5-di-t-butyl-4-hydroxyanisole (5) Phenolic compounds having the formula

wherein Q is as hereinbefore defined.
Illustrative examples of such compounds are
4,4′-thiobis-(2-t-butyl-5-methylphenol)
4,4′-thiobis-(2-t-butyl-6-methylphenol)
2,2′-thiobis-(6-t-butyl-4-methylphenol)
4,4′-thiobis-(2-methyl-5-t-butylphenol)

(6) Phenolic compounds having the formula

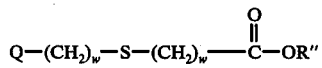

wherein Q, R″ and w are as hereinbefore defined.
Illustrative examples of such compounds are
octadecyl-(3,5-dimethyl-4-hydroxybenzylthio)-acetate
dodecyl-(3,5-di-t-butyl-4-hydroxybenzylthio)-propionate.

(7) Phenolic compounds having the formula

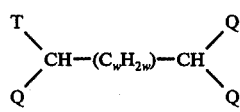

wherein
T is hydrogen
Q and w are as defined above.
Illustrative examples of such compounds are
1,1,3-tris(3,5-dimethyl-4-hydroxyphenol)-propane
1,1,3-tris(5-t-butyl-4-hydroxy-2-methylphenyl)-butane
1,1,5,5-tetrakis-(3′-t-butyl-4′-hydroxy-6′-methylphenyl)-n-pentane.

(8) Phenolic compounds having the formula

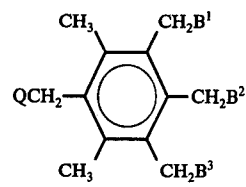

wherein
$B^1$, $B^2$, $B^3$ are hydrogen, methyl or Q provided that when $B^1$ and $B^3$ are Q then $B^2$ is hydrogen or methyl and when $B^2$ is Q then $B^1$ and $B^3$ are hydrogen or methyl; and
Q is as hereinbefore defined.
Illustrative examples of such compounds are
1,4-di(3,5-di-t-butyl-4-hydroxybenzyl)-2,3,5,6-tetramethylbenzene.
1,3,5-tri(3,5-di-t-butyl-4-hydroxybenzyl)-2,4,6-trimethylbenzene.

(9) Phenolic compounds having the formula

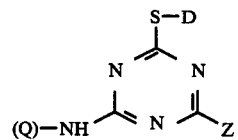

wherein
Z is NHQ, —S—D or —O—Q
D is alkyl group having from 6–12 carbon atoms or —($C_wH_{2w}$)—S—R″
Q, R″ and w are as hereinbefore defined.
Illustrative examples of such compounds are 2,4-bis-(n-octylthio)-6-(3,5-di-t-butyl-4-hydroxyanilino)-1,3,5-triazine
6-(4-hydroxy-3-methyl-5-t-butylanilino)-2,4-bis-(n-octylthio)-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine
6-(4-hydroxy-3,5-di-t-butylanilino)-4-(4-hydroxy-3,5-di-t-butylphenoxy)-2-(n-octylthio)-1,3,5-triazine
2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

(10) Phenolic compounds having the formula

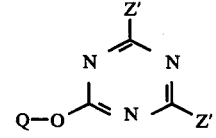

wherein
Z′ is —O—Q, —S—d or —S—($C_wH_{2w}$)—SD,
Q, D and w are as hereinbefore defined.
Illustrative examples of such compounds are 2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine 6-(4-hydroxy-3,5-di-t-butylphenoxy)-2,4-bis-(n-octylthioethylthio)-1,3,5-triazine
6-(4-hydroxy-3-methylphenoxy)2,4-bis-(n-octatylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1-3,5-triazine
2,4-bis-(4-hydroxy-3,5-di-t-butylphenoxy)-6-(n-dodecylthioethylthio)-1,3,5-triazine The above phenolic triazine stablizers are more fully described in U.S. Pat. No. 3,225,191.

(11) Phenolic compounds having the formula

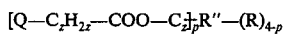

wherein p is an integer from 2 to 4 and
R''' is a tetravalent radical selected from aliphatic hydrocarbons having from 1 to 30 carbon atoms aliphatic mono and dithioethers having from 1 to 30 carbon atoms aliphatic mono and thiethers having from 1 to 30 carbon atoms
z is an integer from 0 to 6
R and Q are as hereinbefore defined.
Illustrative examples of such compounds are

Sub-Class I n-Octadecyl 3-(3,5-di-t-butyl-4-hydroxyphenyl)-propionate
n-Octadecyl 2-(3,5-di-t-butyl-4-hydroxyphenyl)-acetate
n-Octadecyl 3,5-di-t-butyl-4-hydrobenzoate
n-Hexyl 3,5-di-t-butyl-4-hydroxyphenylbenzoate
n-Dodecyl 3,5-di-t-butyl-4-hydroxyphenylbenzoate
Neo-dodecyl 3-(3,5-di-t-butyl-4-hydroxyphenyl)-propionate
Dodecyl β-(3,5-di-t-butyl-4-hydroxyphenyl)-propionate
Ethyl α-(4-hydroxy-3,5-di-t-butylphenyl)-isobutyrate
Octadecyl α-(4-hydroxy-3,5-di-t-butylphenyl)-isobutyrate
Octadecyl α-(4-hydroxy-3,5-di-t-butylphenyl)-propionate;

Sub-class II 2-(n-octhylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl)acetate
Diethyl glycol bis-[3-(3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate;

Sub-class III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl]propionate
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate]

The above phenolic ester stabilizers of sub-classes I, II and III are more fully described in U.S. Pat. No. 3,330,859, U.S. patent applications Ser. No. 354,464, filed Mar. 24th, 1964 which issued as U.S. Pat. No. 3,441,575 and Ser. No. 359,460, filed Apr. 13th, 1964 which issued in a Continuation-in-Part application as U.S. Pat. No. 3,644,482, respectively.

(12) Phenolic compounds having the formula

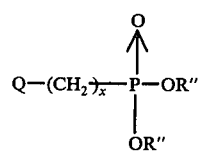

where x is an integer of 1 or 2;
Q and R" are as hereinbefore defined.
Illustrative examples of such compounds are Di-n-octadecyl 3,5-di-t-butyl-4-hydroxybenzylphosphonate
Di-n-octadecyl 3-t-butyl-4-hydroxy-5-methylbenzylphosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexadecyl 3,5-di-t-butyl-4-hydroxybenzylphosphonate
Di-n-decosyl-3,5-di-t-butyl-4-hydroxybenzylphosphonate
Di-n-octadecyl 3,5-di-t-butyl-4-hydroxybenzylphosphonate.

The above di-(higher)alkyl phenolic phosphonates are more fully described in U.S. Pat. No. 3,281,505.
(13) Phenolic compounds having the formula

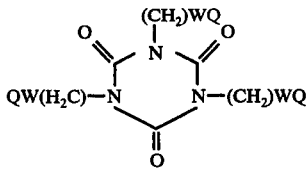

wherein W and Q are defined above.
Illustrative examples of such compounds are:

tris-(3,5-di-t-butyl-4-hydroxybenzyl)isocyanurate
tris-(3-t-butyl-4-hydroxy-5-methylbenzyl)isocyanurate The above hydroxyphenylalkenyl isocyanurates are more fully described in U.S. Pat. No. 3,531,483.
The above phenolic hydrocarbon stabilizers are known and many are commercially available.
While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.
Further examples of antioxidants are those of the aminoaryl series for instance aniline and naphthylamine derivatives as well as their heterocyclic derivatives such as:

phenyl-1-naphthylamine
phenyl-2-naphthylamine
N,N'-diphenyl-p-phenylenediamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include (a) 2-(2'hydroxyphenyl)benzotriazoles, for instance 5'-methyl; 3',5'-di-t-butyl; 5'-t-butyl; 5-chloro-3',5'-di-t-butyl; 5-chloro-3'-t-butyl-5'-methyl; 3'-sec.butyl-5'-tert.butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbomethoxyethyl; 5-chloro-3',5'-di-t-amyl derivatives;
(b) 2,4-bis-(2'-hydroxyphenyl)-6-alkyl-S-triazines, for instance the 6-ethyl or 6-undecyl derivatives;
(c) 2-hydroxybenzophenones, for instance the 4-hydroxy, 4-methoxy, 4-octoxy-, 4-decyloxy-, 4-dodecyloxy, 4,2',4'-trihydroxy or 2'-hydroxy-4,4'-dimethoxy derivatives;
(d) 1,3-Bis(2'-hydroxybenzoyl)-benzenes for instance, 1,3-bis-(2'-hydroxy-4'-hexyloxybenzoyl)benzene 1,3-bis-(2'-hydroxy-4'-octoxybenzoyl)benzene 1,3-bis-(2'-hydroxy-4'-dodecyloxybenzoyl)benzene;
(e) Aryl esters from optionally substituted benzoic acids such as phenylsalicylate, oytylphenylsalicylate, dibenzoyl resorcinol, bis-(4-tert.butylbenzoyl) resorcinol, benzoylresorcinol and 3,5-di-tert.butyl-4-hydroxy-benzoic acid-2,4-di-tert-butyl phenyl ester and - octadecyl ester and -2-methyl-4,6-di-tert.butyl phenyl ester;
(f) Acrylates, for instance α-Cyano-β,β-diphenylacrylic acid ethyl- or iso-octyl ester, α-carbomethoxy-cinnamic acid methyl- or butyl ester and N-(β-carbomethoxyvinyl)-2-methyl indoline;
(g) Nickel compounds as nickel complexes of 2,2'-thio-bis-(4-tert, octylphenol), for instance the 1:1 and 1:2 complexes, optionally having other ligands such as n-butylamine, triethanolamine or N-cyclohexyl-diethanolamine; nickel complexes of bis-(4-tert. octylphenyl) sulphone such as the 2:1 complex, optionally having other ligands such as 2-ethylcaproic acid; nickel dibutyl dithiocarbamates; nickel salts of 4-hydroxy-3,5-di-tert.butylbenzylphosphonic acid mono-alkyl esters such as the methyl-, ethyl- or butyl esters; the nickel complex of 2-hydroxy-4-methylphenyl-undecylketonoxime; and nickel-3,5-di-tert.butyl-4-hydroxy benzoate; and
(h) Oxalic acid diamides, for instance 4,4'-dioctyloxyoxanilide, 2,2'-dioctyloxy-5,5'-di-tert.butyl-oxanilide, 2,2'-di-dodecyloxy-5,5'-di-tert.butyl oxanilide, 2-ethoxy-5-tertiarybutyl-2'-ethyl-oxanilide, 2-ethoxy-2'-ethyl-oxanilide, mixtures of o- nad p- methoxy and ethoxy- di-substituted oxanilides and the compound of formula:

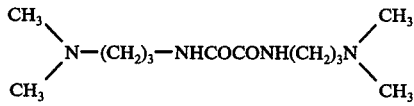

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert. butylphenyl)phosphite.
Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.
Suitable polyamide stabilisers include copper salts in combination with iodides and/or further phosphorus compounds and salts of bivalent manganese.
Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolefine formulations.

The compounds of formula I are mostly new compounds; however those compounds in which $R_1$ and $R_2$ are methyl residues, Y is hydrogen and $R_3$ is hydrogen, a methyl or an ethyl residue have been disclosed in the article by E. I. Leykoeva et al., Khim. Farm. Zh. 1970, 192 (2) 342-5.

The present invention therefore provides compounds having the formula:

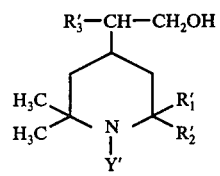

II and salts thereof, wherein $R_1'$, $R_2'$, $R_3'$ and Y' have the same significance as $R_1$, $R_2$, $R_3$ and Y respectively with the proviso that when $R_1'$ and $R_2'$ are each a methyl residue and Y' is hydrogen, then $R_3'$ is not hydrogen or a methyl or an ethyl residue.

Subject to this proviso the preferred substituents $R_1$, $R_2$, $R_3$ and Y' are those indicated hereinbefore.

The present invention also provides a first process of producing a compound of formula II comprising reacting a compound having the formula:

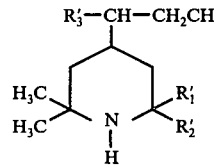

III wherein $R_1'$, $R_2'$ and $R_3'$ have their previous significance with a compound IV capable of introducing the substituent Y' at the nitrogen atom of the compound of formula III.

When the substituent Y' in the compound of formula II is an alkyl, alkenyl, alkynyl or aralkyl residue, the compound of formula III may be conveniently reacted with the corresponding alkyl, alkenyl, alkynyl or aralkyl halide, preferably the corresponding bromide. Alternatively, these derivatives may be obtained by means of a Leuckart or Wallach reaction.

When substituent Y' in the compound of formula II is

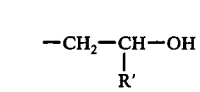

such components may be produced by the treatment of a corresponding compound of formula III with a compound of formula

IV wherein R' has its previous significance.

To produce a compound of formula II wherein the substituent Y' is the radical O, the corresponding compound of formula III may be oxidised with a peroxide, such as hydrogen peroxide, optionally in the presence of pertungstic acid, or with a per-acid such as performic or peracetic acid. In a modification of this oxidation reaction, the starting material may be the corresponding >N-lower alkyl compound rather than the >NH compound of formula III. By the term "lower alkyl" when used in the specification and claims we mean an alkyl residue having from 1 to 4 carbon atoms.

The present invention also provides a second process of producing a compound of formula II comprising reducing a compound having the formula:

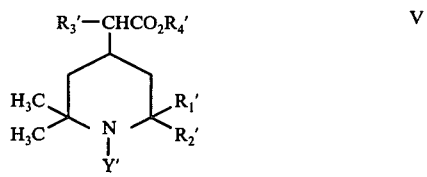

V wherein $R_1'$, $R_2'$ and $R_3'$ have their previous significance, $R_4'$ is hydrogen or an alkyl residue having from 1 to 6 carbon atoms and Y' has its previous significance except that it cannot be O or an unsaturated residue.

The reaction may be conveniently effected using lithium aluminum hydride or sodium in ethanol as the reducing agent. Alternatively, the reaction may be carried out using a catalytic hydrogenation technique, optionally in the presence of a solvent inert under the reaction conditions, and preferably in the presence of a catalyst such as ruthenium, rhenium heptoxide or copper barium chromite.

Compounds of formula V are disclosed in our previous British Patent Nos. 1,398,412 and 1,398,414.

Salts of the compounds of formula II may be produced by reacting the corresponding acid with a compound of formula II in an inert solvent, conveniently at ambient temperature, although higher temperatures may be employed if desired.

Some Examples will now be given. Parts and percentages shown therein are by weight unless otherwise stated.

EXAMPLE 1

A solution of 60 parts by weight of ethyl (2,2,6,6-tetramethylpiperidinyl-4)acetate in 250 parts by volume of dry benzene was added with stirring at room temperature over 1½ hours to a suspension of 10 parts by weight of lithium aluminium hydride in 250 parts by volume of dry ether. The resulting suspension was heated to reflux for 3 hours, then cooled to room temperature and 100 parts by volume of water were then added over 20 minutes. The solid precipitate was collected by filtration and washed with 2 × 100 parts by volume of ether. The ether washings were bulked with the liquors from the reaction and the organic portion were separated, dried over magnesium sulphate, and the solvent removed by distillation in vacuo to give a white crystalline solid. This was washed with petroleum ether (boiling range 40°–60°) and collected by filtration. Thus 46.3 parts by weight (95% of theory yield of 2-(2',2',6',6'-tetramethylpiperidinyl-4')-ethyl alcohol were obtained, melting at 67°–9° C.

The compound so obtained proved an effective stabiliser against degradation by light when incorporated into polypropylene.

EXAMPLE 2

20 parts by volume of 30% hydrogen peroxide were added with stirring over 15 minutes at room temperature to a solution of 9.25 parts by weight of 2-(2',2',6',6'-tetramethylpiperidinyl-4') ethyl alcohol in 40 parts by volume of 75% aqueous ethanol containing 0.2 parts by weight of dodeca-tungstophosphoric acid. The solution was then stirred at room temperature for a further 24 hours, then it was saturated with sodium chloride and extracted with 4 × 50 parts by volume of ether. The ether extracts were bulked and dried over magnesium sulphate and the ether removed by distillation.

Recrystallisation of the solid residue from petroleum ether (boiling range 60° – 80° C.) give 5 parts by weight of orange coloured crystals of 2-(1-oxyl-2',2',6',6'-tetramethylpiperidinyl-4') ethyl alcohol, melting at 64° – 65° C. and having the following elemental analysis by weight:

|  | C | H | N |
|---|---|---|---|
| Found | 66.26 | 10.93 | 6.88 % |
| Required for $C_{11}H_{22}NO_2$ | 66.00 | 11.00 | 7.00 % |

EXAMPLE 3

A mixture of 9.2 parts by weight of 2-(2',2',6',6'-tetramethylpiperidinyl-4') ethyl alcohol, 4.8 parts by volume of 36% aqueous formaldehyde and 5.3 parts by volume of 98% formic acid was heated at 100° C. with stirring for 4 hours. The solution was cooled, added to 50 parts by volume of water and made alkaline with 46% aqueuous sodium hydroxide. The resulting oil was extracted with ether (3 × 50 parts by volume) the combined ether extracts were dried over magnesium sulphate and the ether removed by distillation.

The resulting oil was purified by distillation (108°–110° C./0.8 mm.Hg.) to give 5.6 parts by weight of 2-(1',2',2',6',6'-pentamethylpiperidinyl-4') ethyl alcohol having the following elemental analysis by weight:

|  | C | H | N |
|---|---|---|---|
| Found | 72.05 | 12.50 | 7.00 % |
| Required for $C_{12}H_{25}NO$ | 72.31 | 12.64 | 7.03 % |

EXAMPLE 4

A solution of 7.4 parts by weight of 2-(2',2',6',6'-tetramethylpiperidinyl-4') ethyl alcohol in 25 parts by volume of allyl bromide was heated at reflux for 18 hours. The precipitate was filtered off and the allyl bromide removed by distillation to give an oil which was purified by distillation to give 2.8 parts by weight of 2-(1-allyl-2',2',6',6'-tetramethylpiperidinyl-4') ethyl alcohol, boiling at 150° C./12mm. and having the following elemental analysis by weight:

|  | C | H | N |
|---|---|---|---|
| Found | 74.09 | 11.81 | 5.95 % |
| Required for $C_{14}H_{27}NO$ | 74.61 | 12.08 | 6.21 % |

EXAMPLE 5

A mixture of 11.1 parts by weight of 2-(2',2',6',6'-tetramethylpiperidinyl-4') ethyl alcohol and 5.1 parts by weight of benzyl bromide was heated at 100° C. for 2 hours. The resulting mass was cooled and poured into 100 parts by volume of water. This was extracted with ether (3 × 50 parts by volume) and the combined ether extracts were dried.

The ether was removed by distillation and the residual oil purified by distillation to give 3.4 parts by weight of 2(1'-benzyl-2',2'-6',6'-tetramethylpiperidinyl-4') ethyl alcohol, boiling at 165° C./0.4mm. and having the following elemental analysis by weight:

|  | C | H | N |
|---|---|---|---|
| Found | 78.74 | 10.66 | 4.85 % |
| Required for $C_{18}H_{29}NO$ | 78.49 | 10.61 | 5.09 % |

EXAMPLE 6

A solution of 11.1 parts by weight of 2-(2',2',6',6'-tetramethylpiperidinyl-4') ethyl alcohol and 3.6 parts by weight of 3-bromopropyne in 100 parts by volume of ethyl alcohol was heated at reflux for 18 hours — the resulting suspension was distilled and the residue was dissolved in water (100 parts by volume). The oily precipetate was extracted with ether (3 × 50 parts by volume), the combined ether extracts were dried and the ether removed by distillation.

The residual oil was distilled to give 2-(1'-propargyl-2',2',6',6'-tetramethylpiperidinyl-4') ethyl alcohol boiling at 136° C./0.2mm.Hg. and having the following elemental analysis by weight:

|  | C | H | N |
|---|---|---|---|
| Found | 75.14 | 11.50 | 6.51 % |
| Required for $C_{14}H_{25}NO$ | 75.28 | 11.28 | 6.27 % |

EXAMPLE 7

A mixture of 11.1 parts by weight of 2-(2',2',6',6'-tetramethylpiperidinyl-4') ethyl alcohol and 5.8 parts by weight of n-bromooctane were heated at 100° C. for 36 hours.

The product was worked up as for Example 5, to give 2[1' n-octyl)-2',2',6',6',-tetramethylpiperidinyl-4'] ethyl alcohol, boiling at 162°–165° C./0.2mm. and having the following elemental analysis by weight:

| | N |
|---|---|
| Found | 4.74 % |
| Required for $C_{19}H_{39}NO$ | 4.71 % |

EXAMPLES 8-11

Testing in polypropylene film 38 parts of polypropylene were homogenised with 0.076 parts of n-octadecyl-β(4'-hydroxy-3',5'-t-butyl-phenyl) propionate in a kneading machine over a period of 3 minutes at 200° C. 0.19 parts of the product of Example 11 was then added and homogenisation continued for another 7 minutes.

This composition was compression mouled into films of 0.1 mm thickness at 260° C for 6 minutes and the films so obtained were then quenched in cold water.

A section measuring 44 × 100 mm separated from the 0.1 mm annealed polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3,100 Angstrom units; the blacklight lamps were 2 feet long, 20-watt ultraviolet lamps characterised by a peak emission of 3,500 Angstrom units. The sample was rotated concentrically about the bank of lamps so that the radiation therefrom was uniformly distributed over the section under test.

The exposed sample was examined periodically and portions of it tested for the percent/elongation at break, the time at which the sample reached 50% of the initial elongation at break was noted.

The results obtained including data relating to other compositions of the invention are set out in the following Table:

| Ex. | Product | Factor T/TC Time to 50% of initial elongation at break Time to 50% of initial elongation at break for control |
|---|---|---|
| 8 | 2(2',2', 6',6'-Tetramethylpiperidinyl-4')ethyl alcohol | 2.4 |
| 9 | 2(1',2',2',6',6'-Pentamethylpiperidinyl-4')ethyl alcohol | 4.7 |
| 10 | 2(1'-Oxyl-2',2',6',6'-tetramethyl-piperidinyl-4')ethyl alcohol | 4.3 |
| 11 | 2(1'-Benzyl-2',2',6',6'-tetramethyl-piperidinyl-4')ethyl alcohol | 1.7 |

I claim:

1. A composition comprising an organic material and, as stabiliser, a stabilizing amount of a compound having the formula:

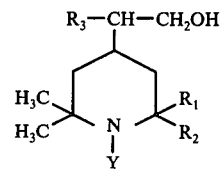

I and salts thereof, wherein $R_1$ and $R_2$ are the same or different and each is an alkyl residue having from 1 to 12 carbon atoms or $R_1$ and $R_2$, together with the carbon atom to which they are bound, form a cycloalkyl residue having from 5 to 12 carbon atoms in the ring, Y is O; hydrogen, a straight- or branched alkyl residue having from 1 to 20 carbon atoms, an alkenyl or alkynyl residue having from 3 to 12 carbon atoms, an aralkyl residue having from 7 to 12 carbon atoms or a group having the formula:

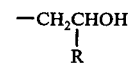

wherein R is hydrogen, or a methyl or phenyl residue and $R_3$ is hydrogen or a straight- or branched chain alkyl residue having from 1 to 12 carbon atoms.

2. A composition as claimed in claim 1 wherein $R_1$ and $R_2$ are each a methyl residue.

3. A composition as claimed in claim 1 wherein Y is a methyl residue, hydrogen or O.

4. A composition as claimed in claim 1 wherein $R_3$ is hydrogen.

5. A composition as claimed in claim 1 wherein the salt is a phosphate, carbonate, chloride, acetate, stearate, maleate, citrate, tartrate, oxalate, benzoate or substituted carbamate.

6. A composition as claimed in claim 1 wherein the organic material is low- or high density polyethylene or polypropylene, polystyrene, a polymer of butene-1, pentene-1, 3-methylbutene-1, hexene-1, 4-methylpentene-1, 4-methylhexene-1, 4,4-dimethylpentene-1 or a co- or ter- polymer of ethylene or propylene.

7. A composition as claimed in claim 1 wherein the organic material is a natural or synthetic polymer.

8. A composition as claimed in claim 7 wherein the synthetic polymer is polyvinyl chloride, polyvinylidene chloride, a vinyl chloride copolymer, polyvinyl acetate or a condensation polymer derived from ether, ester derived from carboxylic, sulphonic or carbonic acids amide or urethane compounds.

9. A composition as claimed in claim 1 wherein the amount of the compound of formula I is within the range of from 0.1% to 2% by weight based on the weight of untreated organic material.

10. A composition as claimed in claim 1 wherein the composition consists of a binary, tertiary or multi-component composition containing, as stabiliser, a compound of formula I together with one or more functional additives for polymers.

11. A composition as claimed in claim 10 wherein the functional additive is an antioxidant of the phenol or amine type, a U.V. absorber or light protectant, a phosphite stabiliser.

12. A composition as claimed in claim 7 wherein the synthetic polymer is a polyvinyl acetal, a polyacrylate, a polyamide, a urea- formaldehyde or melamine- formaldehyde resin or a cellulose plastic.

13. A composition as claimed in claim 1 comprising polypropylene and the stabilizer 2-(2',2',6',6',6'-tetramethylpiperidinyl-4')-ethyl alcohol.

* * * * *